US009421290B2

(12) United States Patent
Victor et al.

(10) Patent No.: US 9,421,290 B2
(45) Date of Patent: Aug. 23, 2016

(54) UV-C CATHETER HUB STERILIZATION AND DATA ACQUISITION SYSTEM

(71) Applicant: TELEFLEX MEDICAL INCORPORATED, Research Triangle Park, NC (US)

(72) Inventors: John C. Victor, Kunkletown, PA (US); David Troy Rowe, Sinking Spring, PA (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 0 days.

(21) Appl. No.: 14/612,033

(22) Filed: Feb. 2, 2015

(65) Prior Publication Data

US 2015/0258230 A1    Sep. 17, 2015

Related U.S. Application Data

(63) Continuation of application No. 14/206,967, filed on Mar. 12, 2014, now Pat. No. 8,946,653.

(60) Provisional application No. 61/783,768, filed on Mar. 14, 2013.

(51) Int. Cl.
*A61L 2/10*    (2006.01)
*G01R 33/07*    (2006.01)
*G06F 19/00*    (2011.01)

(52) U.S. Cl.
CPC . *A61L 2/10* (2013.01); *G01R 33/07* (2013.01); *G06F 19/3406* (2013.01)

(58) Field of Classification Search
USPC .................................................. 250/455.11
See application file for complete search history.

(56) References Cited

U.S. PATENT DOCUMENTS

| 6,212,052 B1* | 4/2001 | Heuer ................... H03K 17/97 361/160 |
| 6,461,568 B1 | 10/2002 | Eckhardt |
| 7,345,476 B2* | 3/2008 | Middelhoek ........... G01R 33/07 324/225 |
| 8,946,653 B2* | 2/2015 | Victor ...................... A61L 2/10 250/455.11 |
| 2002/0146343 A1* | 10/2002 | Jenkins ..................... A61L 2/24 422/24 |
| 2003/0017073 A1* | 1/2003 | Eckhardt .................. A61L 2/10 422/24 |
| 2003/0018373 A1 | 1/2003 | Eckhardt et al. |
| 2007/0057067 A1* | 3/2007 | He .......................... 235/462.45 |
| 2007/0094303 A1* | 4/2007 | Zwingenberger et al. . 707/104.1 |
| 2008/0159908 A1 | 7/2008 | Redmond |
| 2009/0224052 A1* | 9/2009 | Liou .................. G06K 7/10722 235/462.41 |
| 2009/0281523 A1 | 11/2009 | Sacco et al. |

(Continued)

FOREIGN PATENT DOCUMENTS

WO    2009000445 A1    12/2008
WO    2010132429 A2    11/2010

(Continued)

*Primary Examiner* — Phillip A Johnston
(74) *Attorney, Agent, or Firm* — Baker Hostetler LLP (57) ABSTRACT

A hand held hub sterilization and data acquisition device includes a housing having an opening for receiving a medical device, a sterilization chamber formed in the housing, a source of UV radiation disposed within the sterilization chamber for uniform emission of UV-C radiation into the sterilization chamber, and a safety interlock mechanism. The safety interlock mechanism comprises a Hall sensor and a rare earth magnet, and wherein the Hall sensor senses the magnetic field of the magnet when the access door is closed and sends a signal to the user interface indicating a ready state for excitation of the radiation source.

14 Claims, 5 Drawing Sheets

(56) References Cited

U.S. PATENT DOCUMENTS

2009/0315684 A1* 12/2009 Sacco ............... A61M 25/0017
340/10.6
2013/0323120 A1* 12/2013 Ma .................................. 422/24

FOREIGN PATENT DOCUMENTS

| | | |
|---|---|---|
| WO | 2012031147 A2 | 3/2012 |
| WO | 2013181393 A1 | 12/2013 |
| WO | 2014022717 A1 | 2/2014 |

* cited by examiner

UV-C CATHETER HUB STERILIZATION AND DATA ACQUISITION SYSTEM

CROSS REFERENCE TO RELATED APPLICATION

This application is a continuation and the claims the benefit of U.S. patent application Ser. No. 14/206,967, filed Mar. 12, 2014, which claims the benefit of U.S. provisional patent application No. 61/783,768, filed on Mar. 14, 2013, the disclosures of which are hereby incorporated by reference in their entireties.

FIELD OF THE INVENTION

The invention generally relates to ultraviolet irradiation systems, and, more particularly, to methods and systems for catheter hub sterilization and combined data acquisition.

BACKGROUND OF THE INVENTION

Intravascular catheters are an indispensable modern medical device used commonly in many situations and especially in intensive care units (ICUs). The use of these catheters is essential to providing critical therapies and diagnostic services for patients but also places the patient at significant risk for a variety of catheter related bloodstream infections (CRBSI). Any time a catheter is accessed for introduction of therapeutic materials it is possible that foreign pathogenic organisms may also be introduced to the catheter lumen and eventually the bloodstream. Commonly, access sites are required to be scrubbed with solutions containing isopropyl alcohol (IPA) or other antimicrobial agent. These prophylactic measures are often time consuming, minimally effective and poorly complied with.

A need exists for methods and systems of insuring a sterile access site prior to access that minimizes the possibility of the introduction of pathogenic organisms to the catheter lumen.

SUMMARY OF THE INVENTION

The foregoing needs are met by the present invention, wherein according to certain aspects, a hand held hub sterilization and data acquisition device includes a housing having an opening for receiving a medical device, a sterilization chamber formed in the housing, a source of UV radiation disposed within the sterilization chamber for uniform emission of UV-C radiation into the sterilization chamber, and a safety interlock mechanism. The safety interlock mechanism comprises a Hall sensor and a rare earth magnet, and wherein the Hall sensor senses the magnetic field of the magnet when the access door is closed and sends a signal to the user interface indicating a ready state for excitation of the radiation source.

In accordance with other aspects of the present invention, the source of UV radiation for the hand held hub sterilization and data acquisition device is a high voltage tube lamp that produces two ultraviolet wavelengths. In accordance with yet other aspects of the invention, the source of UV radiation for the hand held hub sterilization and data acquisition device is two UV-C lamps comprising a silica quartz envelope to prevent 190 nm wavelength production and provide minimal attenuation to a 254 nm principal wavelength.

In accordance with other aspects of the present invention, the sterilization chamber is a silica quartz tube and an aluminum cylinder may enclose the sterilization chamber to provide high reflection efficiency of outward directed UV-C energy.

In accordance with other aspects of the present invention, the housing may include an access door for receiving the medical device into the sterilization chamber.

In accordance with other aspects of the present invention, the hand held hub sterilization and data acquisition device may include a barcode module. The barcode module may utilize a CMOS 2D imager capable of omnidirectional decoding with regard to code orientation.

In accordance with other aspects of the present invention, the hand held hub sterilization and data acquisition device may receive a catheter extension line with a hub and valve assembly for sterilization.

There has thus been outlined, rather broadly, certain aspects of the present disclosure in order that the detailed description herein may be better understood, and in order that the present contribution to the art may be better appreciated.

In this respect, before explaining at least one embodiment of the invention in detail, it is to be understood that the invention is not limited in its application to the details of the construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
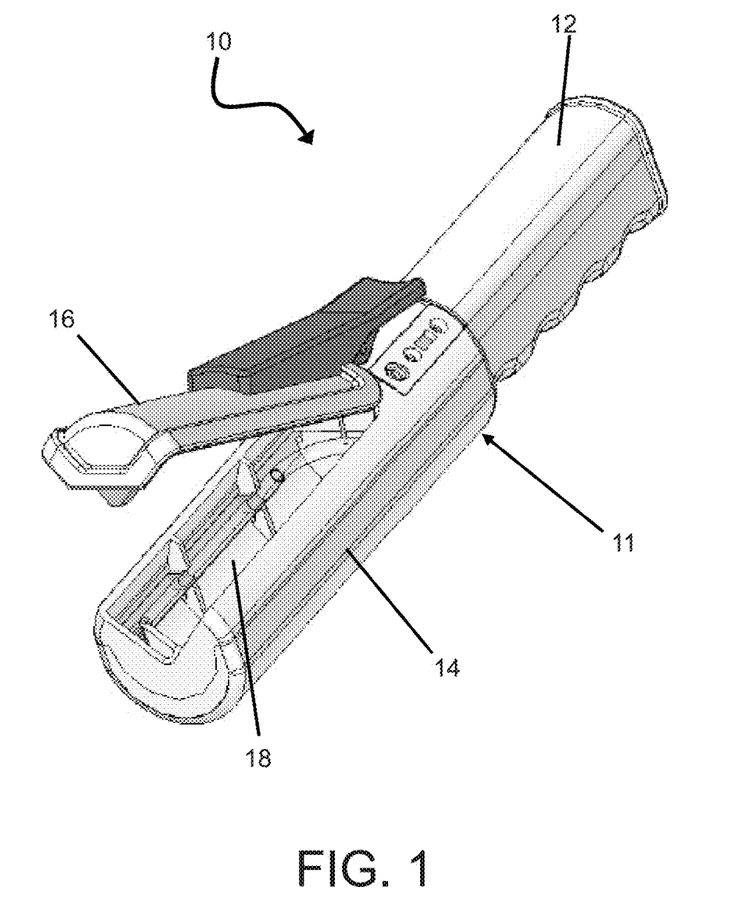
FIG. 1 illustrates a UV-C catheter hub sterilization and data acquisition system, in accordance with aspects of the present disclosure.

FIG. 1 illustrates a hand held hub sterilization and data acquisition device 10 in accordance with aspects of the present invention. The sterilization device 10 may include a housing 11 configured to form a handle portion 12 and a sterilization chamber portion 14. The sterilization portion 14 may include a hinged door 16 for providing access to a UV-C sterilization chamber 18. The chamber 18 may be configured to receive a distal end portion of a catheter extension line including a luer hub and valve assembly, for example.

Figure 2:
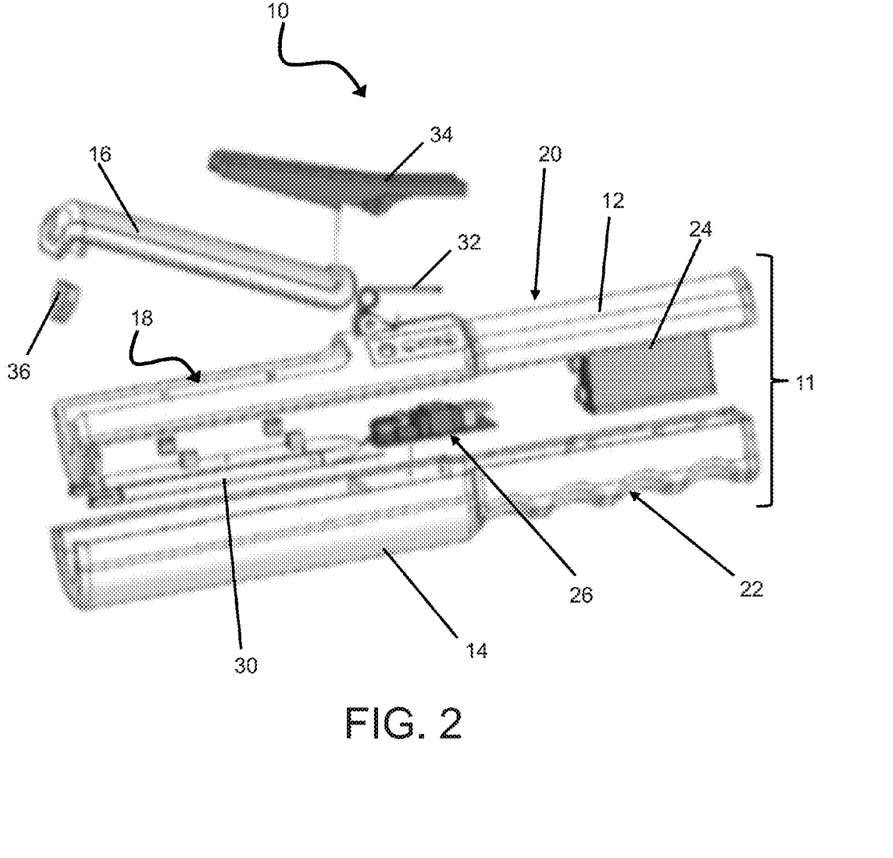
FIG. 2 illustrates an exploded view showing component parts of the system illustrated in FIG. 1, in accordance with aspects of the present disclosure.

As shown in FIG. 2, the housing 11 may be an elongated, essentially hollow structure comprised of a thermoplastic material. The housing 11 may include an upper frame component 20 and a lower frame component 22 that mates with and/or is fastened to the upper frame component 20. The handle portion 12 of the housing 11 may form a substantially hollow area for mounting, securing and protection of critical components, including, for example, a battery 24, various electronic components 26, including a battery charger circuit, a micro controller power regulation circuit, a micro controller, a high voltage lamp ballast and modulation circuit, an output power sensor, and/or various user interface components, such as an LED display or membrane switch assembly). The sterilization chamber portion 14 may be configured to house a UV-C lamp 30 in the sterilization chamber. A spring 32 may cooperate with a rocker arm 34 to bias the hinged door 16 into a closed position. Pressing on a proximal end of the rocker arm 34 to overcome the spring force applied by the spring 32 allows a user to open the hinged door 16 in a clamshell manner, for example. A chamber closure detector 36 may be provided to indicate when the hinged door 16 is closed and the sterilization chamber 18 is sealed and safe for application of a sterilization dose of UV-C radiation. In accordance with other aspects of the present invention, light seals may be provided at or about the interface of the hinged door 16 with the housing 11 to form a substantially light-tight seal of the sterilization chamber 18.

The sterilization device 10 relies on ultraviolet C photonic energy to provide the antimicrobial impact needed to insure a sterile access site. Ultraviolet C photonic energy includes the optical spectrum in the invisible range from ~140 nm to 280 nm wavelength. As shown in FIG. 2, the sterilization device 10 includes a high voltage tube lamp 30 that may produce two ultraviolet wavelengths, 190 nm and 254 nm. In accordance with other aspects of the present invention, the lamp 30 may produce a single wavelength or be configured to produce a broad spectrum source of light. The device 10 provides a sealable irradiating and oxidizing volume adequate to accommodate a catheter extension line including luer hub and valve assembly.

The dual wavelength action may provide two distinct antimicrobial mechanisms to minimize or prevent CRBSI occurrence. The 254 nm wavelength acts directly on the genetic material of the pathogenic organism, cleaving critical molecular bonds and rendering the pathogen incapable of reproduction or normal cellular activity. The second wavelength (190 nm) breaks diatomic oxygen ($O_2$) and fosters the generation of Ozone ($O_3$) from the resulting monatomic oxygen. Ozone rapidly oxidizes any organic material it comes into contact with. In an embodiment using two wavelength radiation, any pathogenic organism not adequately denatured by the 254 nm mechanism may be consumed in oxidation by Ozone.

In addition to providing a superior mechanism of antimicrobial action, the issue of clinician compliance may also be improved. The estimated duration of UV-C/Ozone exposure to insure sterilization is less than 10 seconds. This represents a significant reduction from treatment with isopropyl alcohol, for example, including both application and drying time. The UV-C device 10 may also include an audio and visual progress and process completion indication. This feedback mechanism to the clinician in conjunction with reduced process time may be used to improve procedural compliance by the clinician.

Figure 3:
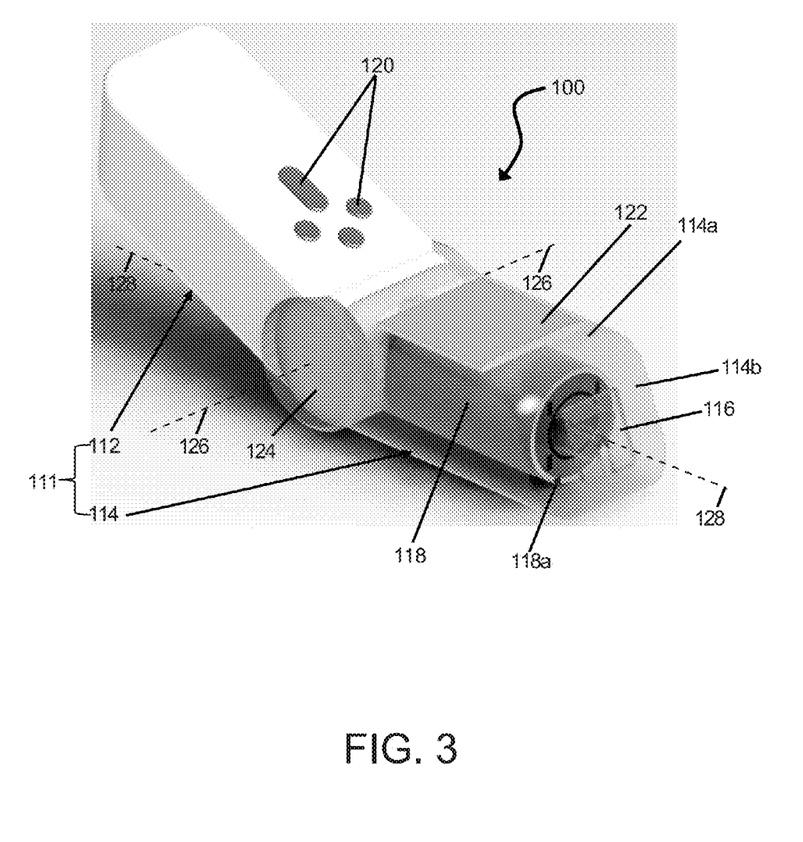
FIG. 3 illustrates another UV-C catheter hub sterilization and data acquisition system, in accordance with aspects of the present disclosure.

FIG. 3 illustrates another embodiment of a hand held hub sterilization device 100 in accordance with aspects of the present invention. The sterilization device 100 may include a body 111 configured to form a handle portion 112 and a sterilization chamber portion 114. The sterilization chamber portion 114 includes a housing 114a that defines an opening at a distal end 114b of the housing 114a. The sterilization chamber portion 114 may include a hinged door 116 at the distal end 114b of the housing 114a for providing access to a UV-C sterilization chamber 118. The sterilization chamber 118 may be configured to receive a distal end portion of a catheter extension line including a luer hub and valve assembly, for example.

The handle portion 112 is attached to the sterilization chamber portion 114 by a hinge portion 124. The handle portion 112 may be rotated relative to the sterilization chamber portion 114, or vice versa, about a first axis 126 of the hinge portion 124. The first axis 126 is perpendicular to a second axis 128 that defines a longitudinal axis of the sterilization chamber portion 114 and the sterilization chamber 118. The hinged door 116 may be moved to open or close the opening at the distal end 114b of the housing 114a, and thereby open or seal the sterilization chamber 118, independent of a rotation the sterilization chamber portion 114 about the first axis 126.

The sterilization chamber 118 may include a one-piece tubular body as illustrated in FIG. 3 that is open at a distal end 118a thereof. The distal end 118a of the sterilization chamber 118 is accessible via the hinged door 116 and the opening at the distal end 114b of the housing 114a. In addition, the distal end 118a of the sterilization chamber 118 is positioned along the second axis 128 relative to, and separate from, the hinged door 116 and the distal end 114b of the housing 114b. A plane including the distal end 114b of the housing, and the hinged door 116 in a closed state, is angled relative to the second axis 128. According to an aspect of the present disclosure the distal end 114b of the housing 114b may extend substantially perpendicular relative to the second axis 128.

In accordance with aspects of the present invention, the device 100 may be configured with two UV-C lamps comprising a silica quartz envelope to prevent 190 nm wavelength/Ozone production and provide minimal attenuation (<5%) to the 254 nm principal wavelength. The sterilization chamber 118 may comprise a silica quartz tube and the UV-C lamps may be mounted into the sterilization chamber 118 in a fashion that evenly distributes the radiation throughout the sterilization chamber 118. The lamps and sterilization chamber 118 may be enclosed by an aluminum cylinder extending along the second axis 128 and processed to provide high reflection efficiency of outward directed UV-C energy, creating an integration effect.

The UV-C sterilization chamber 118 of device 100 may include a safety interlock mechanism for ensuring the user and patient are protected from possible UV-C exposure during the sterilization process. A rare earth magnet may be mounted on the hinged door 116 and a Hall sensor provided at an appropriate location in the sterilization chamber 118 near where the rare earth magnet will be positioned with the hinged door 116 in the closed and sealed position. In this manner, the Hall sensor may sense the magnetic field of the magnet when the hinged door 116 is closed and send a voltage signal to the control electronics indicating when it is safe to proceed with UV-C lamp excitation. The UV-C fluence value (uw/cm2) shall be monitored via a Silicon Carbide photo detector permanently mounted within the sterilization chamber 118.

Input buttons 120, for example, and other user interface features, such as a graphic display 122, may be provided to allow users to interact and control the various functions provided in the hub sterilization device 100 as well as receive or transmit data from the device 100.

Figure 4:
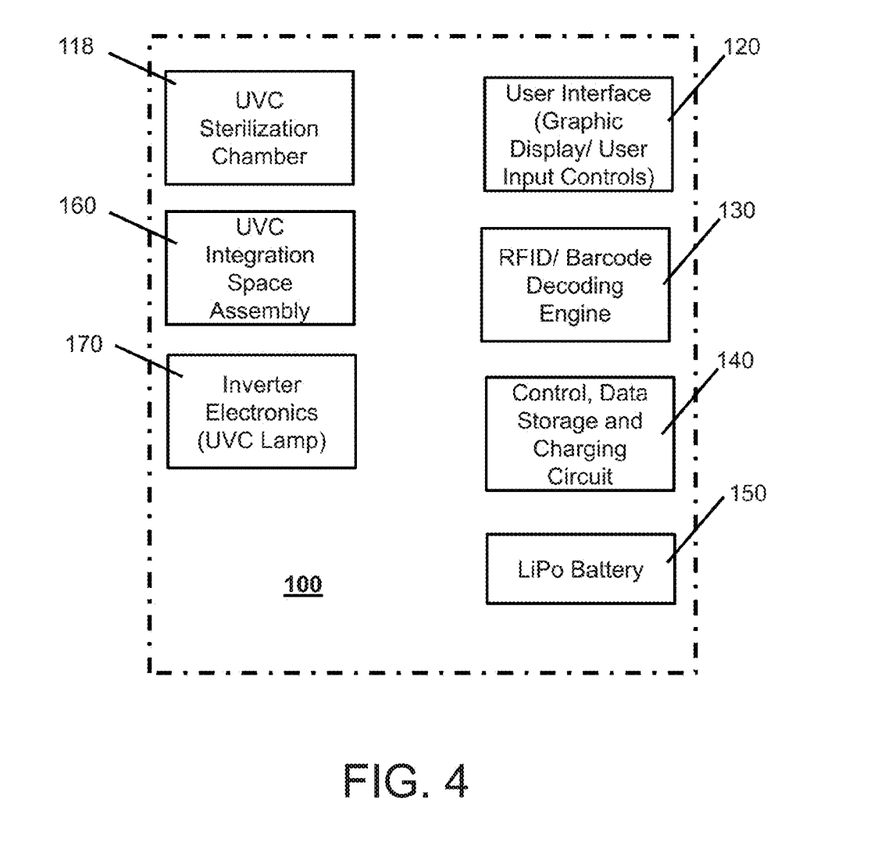
FIG. 4 is a functional diagram of features provided in the system shown in FIG. 3, in accordance with aspects of the present disclosure.

FIG. 4 is a functional diagram illustrating various features that may be provided in the hub sterilization device 100. For example, the device 100 may include the sterilization chamber 118, a user interface consisting of the graphic display 122 and input buttons 120, a radio frequency identification (RFID) and barcode decoding engine 130, a control, data storage and charging circuit 140, a lithium polymer battery 150, a UV-C integration space assembly 160, and high voltage inverter electronics 170 for UV-C lamp excitation.

The device 100 may be capable of decoding all 1D and 2D barcodes associated with user or patient identification parameters. In addition, the barcode engine shall utilize a CMOS 2D imager capable of decoding omni directionally with regard to the code orientation.

Figure 5:
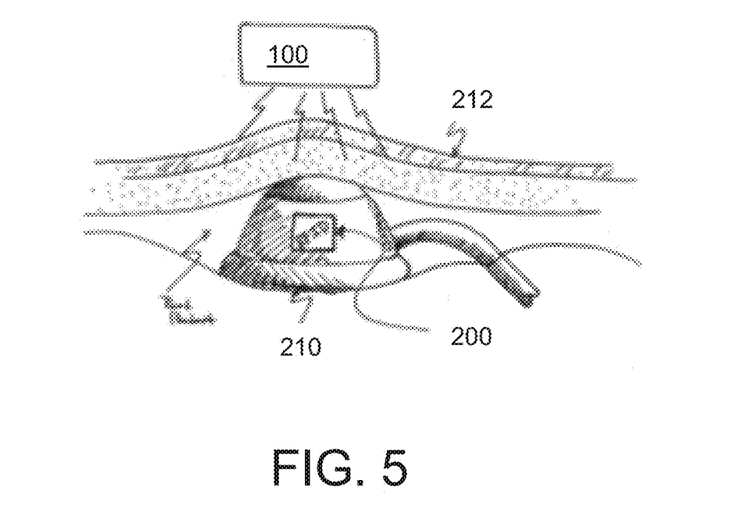
FIG. 5 illustrates the system of FIG. 3 in a state of use, in accordance with aspects of the present disclosure.

In accordance with other aspects of the present invention, the RFID engine shall operate on a 2.4 GHz standard and have read and write capability with all enabled medical devices. RFID chips are robust, passive and small in size. These chips can be programed with various data and be interrogated or reprogramed. As shown in FIG. 5, an RFID chip 200 may be added to medical devices like an implantable subcutaneous port 210. The user may use the RFID function of the device 100 to interrogate the RFID chip 200 on the port 210 below the skin 212 to identify the device's indicated capabilities, for example, pressure injectability. Additional data may be added to the RFID for clinical use. These data could include, but are not limited to, for example, manufacturer's name, product number, lot number, implant date, device capability, patient data, injection history, etc. These data would be saved and/or modified by scanning the device 100 in close proximity to the RFID chip 200, and the data may then be synced with the hospital's Electronic Medical Records (EMR) database.

Data attributed to the RFID enabled device shall include but is not limited to the following: GS1 manufacturer information, Patient ID, Last user ID, Last Use Time and Date, Implant Date, Implant facility ID, Incrementing number of accesses, and Sterilization statistics. Data stored within the device 100 for electronic medical record upload shall include but is not limited to the following: User ID Log with Time and Date stamp, Device ID Log with implant date, Usage log with patient data and Time and Date stamp, Fault condition log, and Sterilization statistics.

The user interface of the device 100 may, for example, provide the following information to a user: battery charge level, fault conditions, including unsafe condition due to possible user/patient UV-C exposure, insufficient UV-C fluence value for adequate sterilization, a barcode read error, an RFID read error, a power failure, and/or a user input error, the sequence state, which may be Ready, Scan User, Scan Patient, Sterilize, UV-C in process (time to complete), Sterilization Complete, Fault.

The sterilization device 100 may be incorporated into a patient care system that includes multiple device charging and download/upload stations, a single device bedside charging and download/upload station, RFID enabled medical devices, such as catheters, ports, or suitable disposable medical devices, for example, device control and data acquisition software, charging station control and electronic medical record data interface software.

It is to be understood that any feature described in relation to any one aspect may be used alone, or in combination with other features described, and may also be used in combination with one or more features of any other of the disclosed aspects, or any combination of any other of the disclosed aspects.

It is to be understood that any feature described in relation to any one aspect may be used alone, or in combination with other features described, and may also be used in combination with one or more features of any other of the disclosed aspects, or any combination of any other of the disclosed aspects.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

The invention claimed is:

1. A hand held hub sterilization and data acquisition device comprising:
   a housing defining an opening at a distal end of the housing;
   a hinged access door positioned on the distal end of the housing;
   a sterilization chamber formed in the housing along a longitudinal axis that extends at an angle relative to a plane including the distal end of the housing;
   a source of UV radiation disposed within the sterilization chamber for uniform emission of UV-C radiation into the sterilization chamber;
   a user interface; and
   a safety interlock mechanism,
   wherein the safety interlock mechanism comprises a rare earth magnet mounted on the hinged access door and a Hall sensor, and
   wherein the hinged access door is closed and the Hall sensor senses a magnetic field of the magnet and sends a signal to the user interface indicating a ready state for excitation of the source of UV radiation.

2. The device of claim 1, wherein the source of UV radiation is a high voltage tube lamp that produces two ultraviolet wavelengths.

3. The device of claim 1, wherein the source of UV radiation is two UV-C lamps comprising a silica quartz envelope to prevent 190 nm wavelength production and provide minimal attenuation to a 254 nm principal wavelength.

4. The device of claim 1, wherein the sterilization chamber is a silica quartz tube.

5. The device of claim 4, further comprising an aluminum cylinder enclosing the sterilization chamber and providing high reflection efficiency of outward directed UV-C energy.

6. The device of claim 1, further comprising an aluminum cylinder enclosing the sterilization chamber and providing high reflection efficiency of outward directed UV-C energy.

7. The device according to claim 1, further comprising a barcode module.

8. The device according to claim 7, wherein the barcode module utilizes a CMOS 2D imager capable of omnidirectional decoding with regard to code orientation.

9. The device according to claim 1, wherein the medical device is a catheter extension line with a hub and valve assembly.

10. The device according to claim 1,
    wherein the Hall sensor is positioned in a first position in the sterilization chamber,
    wherein the hinged access door is closed and the rare earth magnet is positioned in a second position proximate to the first position such that the Hall sensor senses the magnet field of the magnet, and wherein the rare earth magnet is in the second position and the sterilization chamber is sealed.

11. The device according to claim 1, wherein a distal end of the sterilization chamber is positioned along the second axis relative to the hinged door and the distal end of the housing.

12. The device according to claim 1, wherein the distal end of the housing extends substantially perpendicular to the longitudinal axis.

13. The device according to claim 1, further comprising:
a handle portion; and
a hinge portion attaching the housing to the handle portion, wherein the housing is configured to rotate relative to the handle portion about an axis that is perpendicular to the longitudinal axis.

14. The device according to claim 13, wherein the hinged door is configured to move to open and close the sterilization independent of a rotation of the housing about the axis.

* * * * *